United States Patent
Price et al.

(10) Patent No.: US 10,260,946 B2
(45) Date of Patent: Apr. 16, 2019

(54) OPTICOANALYTICAL DEVICES WITH CAPACITANCE-BASED NANOMATERIAL DETECTORS

(71) Applicant: Halliburton Energy Services, Inc., Houston, TX (US)

(72) Inventors: James M. Price, The Woodlands, TX (US); Aditya B. Nayak, Houston, TX (US); David L. Perkins, The Woodlands, TX (US); Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 171 days.

(21) Appl. No.: 15/306,905

(22) PCT Filed: Nov. 13, 2015

(86) PCT No.: PCT/US2015/060525
§ 371 (c)(1),
(2) Date: Oct. 26, 2016

(87) PCT Pub. No.: WO2017/082919
PCT Pub. Date: May 18, 2017

(65) Prior Publication Data
US 2017/0268926 A1 Sep. 21, 2017

(51) Int. Cl.
*G01J 1/46* (2006.01)
*G01J 3/00* (2006.01)
(Continued)

(52) U.S. Cl.
CPC ............. *G01J 3/42* (2013.01); *B82Y 15/00* (2013.01); *G01J 1/46* (2013.01); *G01J 3/00* (2013.01);
(Continued)

(58) Field of Classification Search
CPC ........ G01J 1/46; G01J 3/28; G01J 3/42; G01J 3/32; G01J 3/00; G01N 21/31;
(Continued)

(56) References Cited

U.S. PATENT DOCUMENTS

| 5,922,537 A | 7/1999 | Ewart et al. |
| 6,514,453 B2 | 2/2003 | Vigliotti et al. |

(Continued)

FOREIGN PATENT DOCUMENTS

| WO | 2013169606 A1 | 11/2013 |
| WO | 2014021701 A1 | 2/2014 |

(Continued)

OTHER PUBLICATIONS

Aghaeipour et al. ("Tunable absorption resonances in the ultraviolet for InP nanowire arrays", Optics Express, Nov. 17, 2014, vol. 22, No. 23).*

(Continued)

*Primary Examiner* — Que Tan Le
*Assistant Examiner* — Jennifer D Bennett
(74) *Attorney, Agent, or Firm* — Gilliam IP PLLC (57) ABSTRACT

Optical computing devices may include capacitance-based nanomaterial detectors. For example, an optical computing device may include a light source that emits electromagnetic radiation into an optical train extending from the light source to a capacitance-based nanomaterial detector; a material positioned in the optical train to optically interact with the electromagnetic radiation and produce optically interacted light; and the capacitance-based nanomaterial detector comprising one or more nano-sized materials configured to have a resonantly-tuned absorption spectrum and being configured to receive the optically interacted light, apply a vector related to the characteristic of interest to the optically interacted light using the resonantly-tuned absorption spec- (Continued)

trum, and generate an output signal indicative of the characteristic of interest.

18 Claims, 7 Drawing Sheets

(51) Int. Cl.
  *G01J 3/42* (2006.01)
  *B82Y 15/00* (2011.01)
  *G01N 21/25* (2006.01)
  *G01N 21/31* (2006.01)
  *E21B 49/00* (2006.01)
(52) U.S. Cl.
  CPC ........... *G01N 21/251* (2013.01); *G01N 21/31* (2013.01); *E21B 49/00* (2013.01)
(58) Field of Classification Search
  CPC ........ G01N 21/25; G01N 27/02; G01N 27/22; G01N 21/00; G01N 21/85; G01N 21/55; G01N 21/94; G01N 21/251; E21B 49/00; E21B 49/08; C12M 1/34; B82Y 15/00
  See application file for complete search history.

(56) References Cited

U.S. PATENT DOCUMENTS

| | | |
|---|---|---|
| 6,529,277 B1 | 3/2003 | Weitekamp |
| 6,641,775 B2 | 11/2003 | Vigliotti et al. |
| 6,894,359 B2 | 5/2005 | Bradley et al. |
| 7,305,883 B2 | 12/2007 | Khuri-Yakub et al. |
| 7,449,757 B2 | 11/2008 | Bradley et al. |
| 7,522,040 B2 | 4/2009 | Passmore et al. |
| 7,547,931 B2 | 6/2009 | Star et al. |
| 7,923,801 B2 | 4/2011 | Tian et al. |
| 7,948,041 B2 | 5/2011 | Bryant et al. |
| 7,955,559 B2 | 6/2011 | Joshi et al. |
| 7,956,525 B2 | 6/2011 | Armitage et al. |
| 8,152,991 B2 | 4/2012 | Briman et al. |
| 8,154,093 B2 | 4/2012 | Bradley et al. |
| 8,269,260 B2 | 9/2012 | Tian et al. |
| 8,269,302 B2 | 9/2012 | Tian et al. |
| 8,274,126 B2 | 9/2012 | Tian et al. |
| 8,425,745 B2 | 4/2013 | Briman et al. |
| 8,466,533 B2 | 6/2013 | Tian et al. |
| 8,476,727 B2 | 7/2013 | Tian et al. |
| 8,482,093 B2 | 7/2013 | Tian et al. |
| 8,513,758 B2 | 8/2013 | Tian et al. |
| 8,525,287 B2 | 9/2013 | Tian et al. |
| 8,530,991 B2 | 9/2013 | Tian et al. |
| 8,530,992 B2 | 9/2013 | Tian et al. |
| 8,530,993 B2 | 9/2013 | Tian et al. |
| 8,546,853 B2 | 10/2013 | Tian et al. |
| 8,558,286 B2 | 10/2013 | Tian et al. |
| 8,643,064 B2 | 2/2014 | Tian et al. |
| 9,103,716 B2 | 8/2015 | Tunheim et al. |
| 9,182,355 B2 | 11/2015 | Tunheim et al. |
| 2003/0134433 A1 | 7/2003 | Gabriel et al. |
| 2004/0132070 A1 | 7/2004 | Star et al. |
| 2011/0259082 A1 | 10/2011 | Remskar et al. |
| 2011/0287977 A1 | 11/2011 | Cai et al. |
| 2012/0282594 A1 | 11/2012 | Chen et al. |
| 2013/0013211 A1 | 1/2013 | Kumar |
| 2013/0031964 A1 | 2/2013 | Tunheim et al. |
| 2013/0031970 A1 | 2/2013 | Freese et al. |
| 2013/0031971 A1 | 2/2013 | Freese et al. |
| 2013/0031972 A1 | 2/2013 | Freese et al. |
| 2013/0032333 A1 | 2/2013 | Freese et al. |
| 2013/0032334 A1 | 2/2013 | Freese et al. |
| 2013/0032340 A1 | 2/2013 | Freese et al. |
| 2013/0032344 A1 | 2/2013 | Freese et al. |
| 2013/0032345 A1 | 2/2013 | Freese et al. |
| 2013/0032545 A1 | 2/2013 | Freese et al. |
| 2013/0033701 A1 | 2/2013 | Tunheim et al. |
| 2013/0140649 A1 | 6/2013 | Rogers et al. |
| 2013/0240837 A1* | 9/2013 | Bandyopadhyay ......................... H01L 31/035227 257/21 |
| 2014/0002111 A1 | 1/2014 | Potyrailo et al. |
| 2014/0015548 A1 | 1/2014 | Naughton et al. |
| 2014/0061449 A1 | 3/2014 | Tunheim et al. |
| 2014/0061513 A1 | 3/2014 | Tunheim et al. |
| 2014/0067268 A1 | 3/2014 | Tunheim et al. |
| 2014/0076549 A1 | 3/2014 | Pelletier et al. |
| 2014/0076550 A1 | 3/2014 | Pelletier et al. |
| 2014/0076551 A1 | 3/2014 | Pelletier et al. |
| 2014/0078499 A1 | 3/2014 | Tunheim et al. |
| 2014/0080172 A1 | 3/2014 | Tunheim et al. |
| 2014/0080223 A1 | 3/2014 | Tunheim et al. |
| 2014/0080224 A1 | 3/2014 | Tunheim et al. |
| 2014/0081594 A1 | 3/2014 | Tunheim et al. |
| 2014/0166274 A1 | 6/2014 | Weiner et al. |
| 2014/0166361 A1 | 6/2014 | Jamison et al. |
| 2014/0166871 A1 | 6/2014 | Jamison et al. |
| 2014/0170025 A1 | 6/2014 | Weiner et al. |
| 2014/0172177 A1 | 6/2014 | Jamison et al. |
| 2014/0252251 A1 | 9/2014 | Tunheim et al. |
| 2014/0255598 A1 | 9/2014 | Simcock et al. |
| 2014/0305900 A1 | 10/2014 | Rogers et al. |
| 2014/0323968 A1 | 10/2014 | Rogers et al. |

FOREIGN PATENT DOCUMENTS

| | | |
|---|---|---|
| WO | 2015047238 A1 | 4/2015 |
| WO | 2015060816 A1 | 4/2015 |

OTHER PUBLICATIONS

Kallempudi, Sreenivasa, A Nanostructured-Nickel Based Interdigitated Capacitive Transducer for Biosensor Applications, 2011.
Bandyopadhyay, Saumil, Nanowire-Based Frequency-Selective Capacitive Photodetector for Resonant Detection of Infrared Radiation at Room Temperature, Journal of Applied Physics 116, 023108 (2014), pp. 1-7.
Ozevin et al., Resonant Capacitive MEMS Acoustic Emission Transducers, 2006.
ISR/WO for PCT/US2015/060525 dated Aug. 29, 2016.

* cited by examiner

OPTICOANALYTICAL DEVICES WITH CAPACITANCE-BASED NANOMATERIAL DETECTORS

BACKGROUND

Optical computing devices, also commonly referred to as "opticoanalytical devices," can be used to analyze and monitor substances in real time. Such optical computing devices will often employ a light source that emits electromagnetic radiation to optically interact with (i.e., reflects from, transmitted through, etc.) a material and an optical processing element to determine quantitative and/or qualitative values of one or more physical or chemical properties of the material. The optical processing element may be, for example, an integrated computational element (ICE) core, also known as a multivariate optical element (MOE). ICE cores are designed to operate over a continuum of wavelengths in the electromagnetic spectrum from the UV to mid-infrared (MIR) ranges, or any sub-set of that region. Electromagnetic radiation that optically interacts with the material is changed and processed by the ICE core to be measured by a detector (e.g., a room temperature infrared (IR) detector), and outputs from the detector can be correlated to the physical or chemical property of the material being analyzed.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure relates to optical computing devices and, more particularly, to optical computing devices that employ capacitance-based nanomaterial detectors.

The embodiments described herein employ various configurations of optical computing devices for the real-time or near real-time monitoring of a material. The optical computing devices described herein optically and otherwise physically apply weighting factors to derived response signals, as opposed to digitally applying the weighting factors using a signal processor and associated software applications. As a result, neural network or linear combinatorial methods of optical measurements may be made in parallel rather than sequentially, thereby resulting in faster sampling times. In some embodiments, the detector portion of the optical computing device is a capacitance-based nanomaterial detector, which may optionally be resonantly-tuned for specifically detecting the electromagnetic radiation having optically interacted with an ICE core and corresponding to the characteristic of interest. In some instances, resonant tuning of the capacitance-based nanomaterial detector may be used to exclude or reject wavelengths of electromagnetic radiation that do not correspond to a characteristic of interest. In alternate embodiments, the capacitance-based nanomaterial detectors may replace the ICE core of the optical computing devices.

As used herein, the term "nano-sized" refers to having at least one dimension less than 100 nm.

As used herein, the term "characteristic" or "characteristic of interest" refers to a chemical, mechanical, or physical property of a material. The characteristic of a material may include a quantitative or qualitative value of one or more chemical constituents or compounds present therein or any physical property associated therewith. Such chemical constituents and compounds may be referred to herein as "analytes." Illustrative characteristics of a material that can be detected with the optical computing devices described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, transmittance, combinations thereof, state of matter (solid, liquid, gas, emulsion, mixtures thereof, etc.), and the like.

As used herein, the term "material," or variations thereof, refers to at least a portion of matter to be tested or otherwise evaluated using the optical computing devices described herein. The material includes the characteristic of interest, as defined above. The material may be any fluid capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders, muds, glasses, mixtures, combinations thereof, and may include, but is not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, breakers, scavengers, stabilizers, clarifiers, detergents, treatment fluids, fracturing fluids, formation fluids, or any oilfield fluid, chemical, or substance commonly found in the oil and gas industry. In some cases, the material may also refer to a solid material such as, but not limited to, rock formations, concrete, cement, solid wellbore surfaces, pipes or flow lines, and solid surfaces of any wellbore tool or projectile (e.g., balls, darts, plugs, etc.).

As used herein, the term "electromagnetic radiation" refers to radio waves, microwave radiation, terahertz, infrared and near-infrared radiation, visible light, ultraviolet light, X-ray radiation and gamma ray radiation.

As used herein, the term "optically interact" or variations thereof refers to the reflection, transmission, scattering, diffraction, or absorption of electromagnetic radiation either on, through, or from one or more processing elements (i.e., an optical processing device), a material being analyzed by the processing elements, or a polarizer. Accordingly, optically interacted light (also referred to as "optically interacted electromagnetic radiation") refers to electromagnetic radiation that has been reflected, transmitted, scattered, diffracted, or absorbed by, emitted, or re-radiated, for example, using a processing element, but may also apply to optical interaction with a material or a polarizer.

As used herein, the terms "optically coupled" and "optically aligned" are used interchangeably and refer to axially and optically aligning optical components of an optical computing device along the optical train of the optical computing device. When optical components of an optical computing device are optically coupled or aligned, for example, electromagnetic radiation that optically interacts with one element of a first optical component array is able to optically communicate with a co-axially aligned element of a second optical component array while a material is being analyzed.

The optical computing devices described herein include at least one capacitance-based nanomaterial detector. The capacitance-based nanomaterial detectors described herein comprise one or more nano-sized materials. As described further herein, the size, shape, and composition, inter alia, of each of the nano-sized materials may be chosen to give the capacitance-based nanomaterial detector a desired absorption spectrum.

The capacitance-based nanomaterial detectors described herein utilize a capacitance mechanism for measuring the incident electromagnetic radiation as compared to the conductance mechanism that IR detectors are based on. Generally, a conductance mechanism relies on photo-excitation of charge carriers across the band gap of a semiconductor material to change the charge transport properties (i.e., the electrical conductance) of the semiconductor material. By contrast, the capacitance mechanism relies on photo-excited electron-hole pairs across the band gap of a nano-sized semiconductor material that alter the local electric field and allow for measuring charge density changes in the nano-sized semiconductor material. Charge density changes occur near instantaneously (e.g., on the order of nanoseconds), while changes to the charge transport properties of a semiconductor material occur much slower (e.g., about three orders of magnitude slower).

Additionally, the capacitance mechanism of detection allows the capacitance-based nanomaterial detectors to tolerate higher temperatures with ample signal-to-noise ratios, which may reduce or eliminate the cooling required for traditional IR detectors. Accordingly, optical computing devices having the capacitance-based nanomaterial detectors may be utilized in higher temperatures (e.g., borehole temperatures in oil and gas operations) without a cooling system.

In some instances, the nano-sized semiconductor materials of the capacitance-based nanomaterial detectors described herein may be chosen to be resonantly-tuned to the incident electromagnetic radiation corresponding to the characteristic of interest, which may increase the sensitivity of the detector. That is, the band gap of the one or more nano-sized semiconductor materials may be configured to correspond to (1) the spectrum of the electromagnetic radiation having optically interacted with an ICE core or (2) an optical processing function that applies a weighting or loading factor to the electromagnetic radiation having optically interacted a material, thereby allowing the capacitance-based nanomaterial detector to have the functionality of both the ICE core and the detector.

The band gap of the nano-sized semiconductor materials may be altered to achieve the desired resonant tuning by (1) changing the composition of the nano-sized semiconductor materials (2) changing the electron confinement in one, two, or three dimensions of the nano-sized semiconductor materials, (3) applying an electric field to the capacitance-based nanomaterial detector, or a combination thereof.

Figure 1:
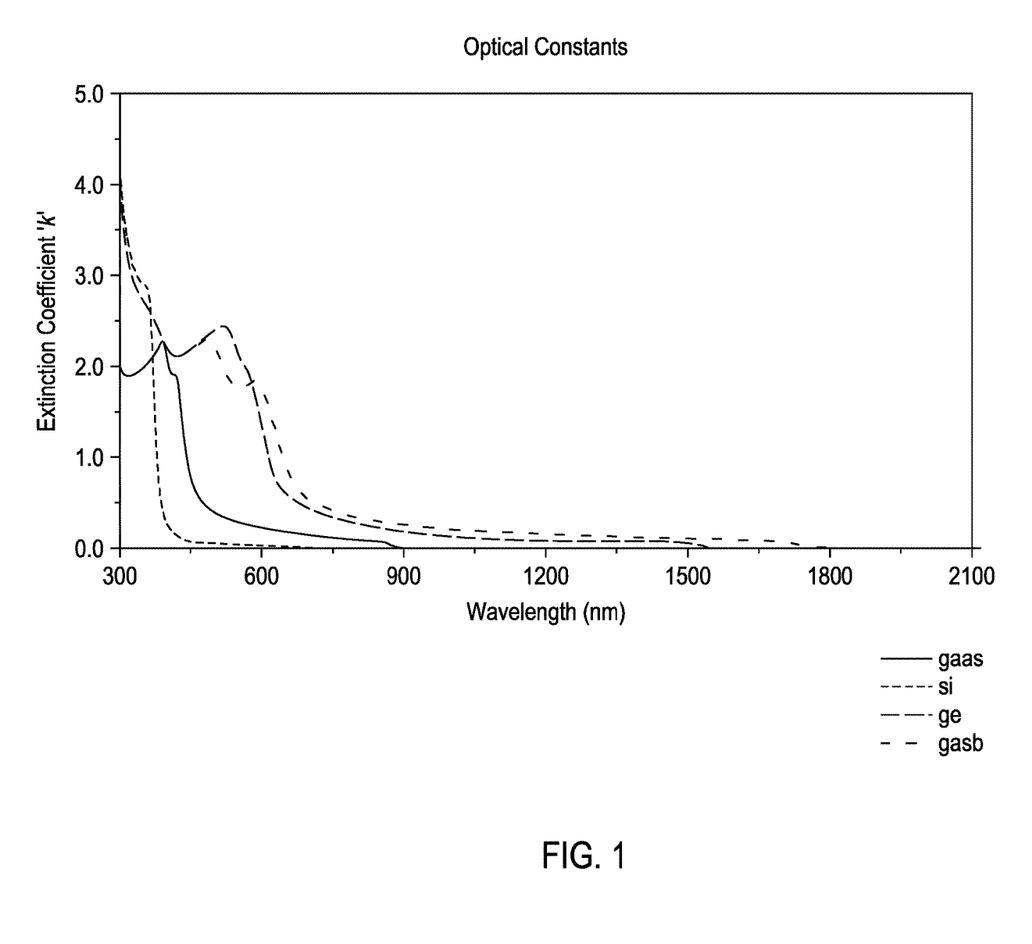
FIG. 1 provides the absorption spectra of silicon (Si), germanium (Ge), and gallium arsenide (GaAs).
Figure 2:
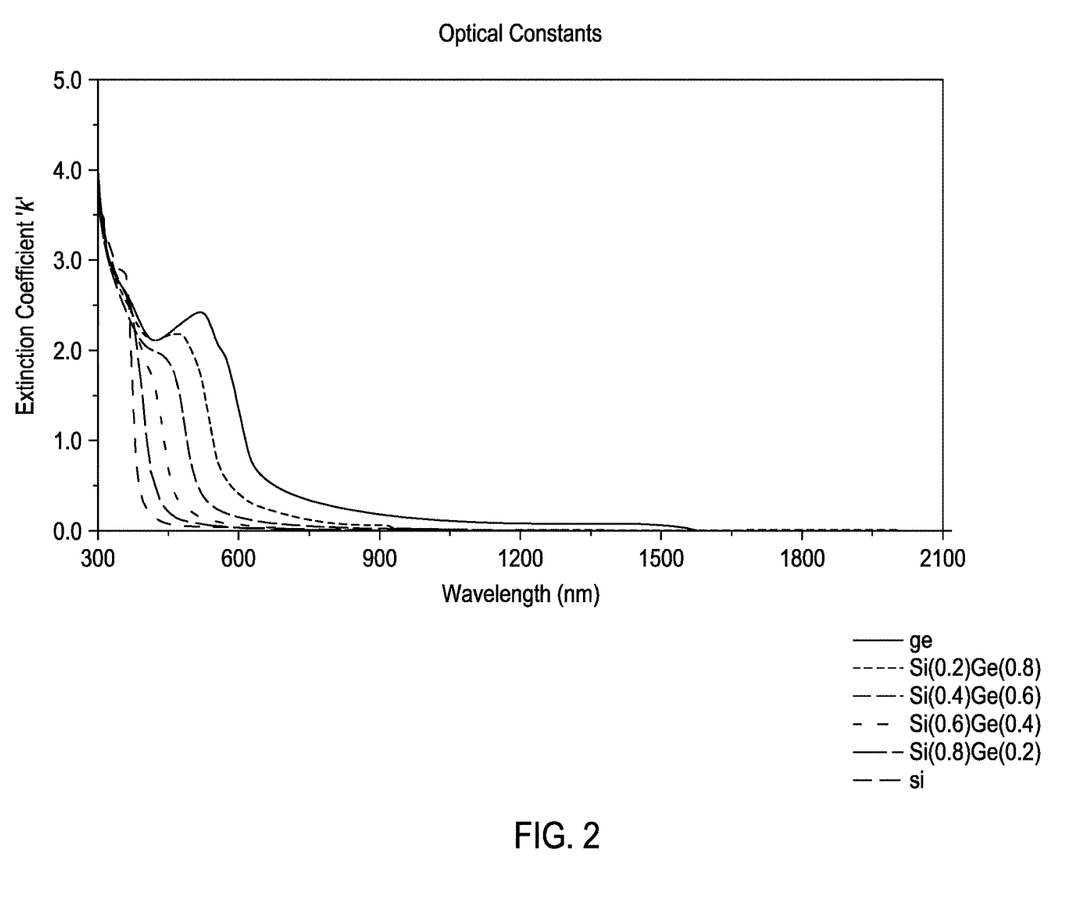
FIG. 2 provides the absorption spectra of $Si_xGe_y$ with varying % Ge illustrating that each have different band gaps in the NIR to visible range.

The chemical composition of a nano-sized semiconductor material affects the band gap that will dictate the wavelength of light that is absorbed. For example, FIG. 1 provides the absorption spectra of silicon (Si), germanium (Ge), gallium arsenide (GaAs), and gallium antimony (GaSb) illustrating that each have different band gaps, which are indicated at the onset of absorption, in the NIR range. Further, the band gap of the nano-sized semiconductor material can be changed by alloying semiconductors together. For example, alloying Si and Ge ($Si_xGe_y$) allows for altering the band gap from 1127 nm to 1850 nm depending on the % Ge. For example, FIG. 2 provides the absorption spectra of $Si_xGe_y$ with varying % Ge illustrating that each have different band gaps in the NIR to visible range.

Exemplary semiconductors and alloys thereof suitable for use in capacitance-based nanomaterial detectors described herein may include, but are not limited to, Si, Ge, $Si_xGe_y$ (x+y=1, 0<x<1), GaAs, GaSb, and the like.

The size and shape of a nano-sized semiconductor material affects its band gap due to quantum confinement. As a result of quantum confinement, the material's band gap will be blue shifted (i.e., shifted to lower wavelengths) ($\Delta E$) according to Equation 1, the eigenvalue solution to Schrodinger's equation for an electron in a periodic quantum confined potential, where $E_g$ is the direct band gap of the bulk semiconductor, $\hbar$ is Plank's constant, m* is the effective mass or the electron in the semiconductor, and L is the size of the confined dimension (i.e., the smallest diameter of the nano-sized semiconductor, for example, the diameter of a nanowire).

$$\Delta E = E_g + \frac{(\pi\hbar)^2}{2m*L^2} \qquad \text{Equation 1}$$

Exemplary shapes for nano-sized semiconductor materials of the capacitance-based nanomaterial detector may include, but are not limited to, films, wires (e.g., elongated structures with an aspect ratio of 5 or greater), rods (e.g., elongated structures with an aspect ratio less than 5), tubes (e.g., hollow wires or rods), stars (e.g., a particle having three or more protrusions extending therefrom, where a protrusion is at least $\frac{1}{5}^{th}$ the diameter of the star) (e.g., nanostars, tetrapods, and the like), particles (e.g., circular, ovular, prolate, and the like), discs, and the like.

In addition to the band gap energy shift ($\Delta E$), the density of states of the band gap is altered by quantum confinement, which manifests as a change in the shape of the absorption spectrum. Increasing the number of dimensions in which the nano-sized semiconductor material is quantum confined increases the density of states of the band gap and, accordingly, sharpens or narrows the shape of the absorption spectrum. For example, a thin film is quantum confined in one dimension and, therefore, has a broader absorption spectrum than a nanowire that is confined in two dimensions.

Therefore, the size and shape of the nano-sized semiconductor material and the corresponding quantum confinement principles may be used to change both the onset and the shape of the absorption, which allows for tuning the absorption spectra of the capacitance-based nanomaterial detector to be resonantly-tuned with the incident electromagnetic radiation (e.g., from the ICE core or the material) corresponding to the characteristic of interest.

A third method of resonant tuning of the capacitance-based nanomaterial detector is applying an electrical field to the nano-sized semiconductor material. For example, an electric field may be applied across a nanowire where the voltage may be adjusted to resonantly tune the absorption spectra of the nanowire with the incident electromagnetic radiation corresponding to the characteristic of interest.

The foregoing three variables may be used independently or in combination to correlate the absorption spectrum of the capacitance-based nanomaterial detector with the incident electromagnetic radiation corresponding to the characteristic of interest.

Figure 3:
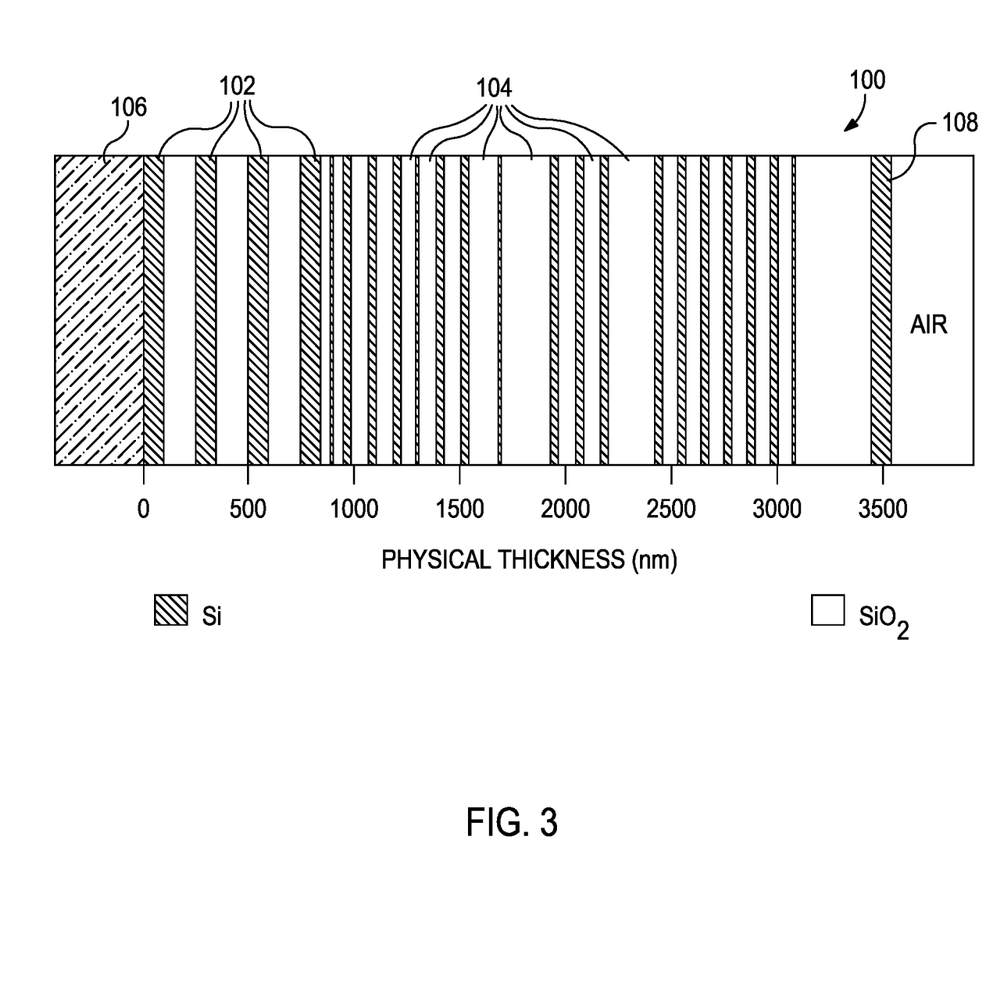
FIG. 3 illustrates an exemplary integrated computation element core according to at least one embodiment described herein.

In some embodiments, the optical computing devices described herein may employ one or more integrated computational element (ICE) cores. In operation, an ICE core is designed to distinguish electromagnetic radiation related to a characteristic of interest of a material from electromagnetic radiation related to other components of the material. With reference to FIG. 3, illustrated is an exemplary ICE core 100 that may be used in the systems described herein. As illustrated, the ICE core 100 may include a plurality of alternating thin film layers 102 and 104, such as silicon (Si) and $SiO_2$ (quartz), respectively. In general, these layers 102, 104 consist of materials whose index of refraction is high and low, respectively. Other examples of materials might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as another optical glass, silica, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 3), the ICE core 100 may include a layer 108 that is generally exposed to the environment of the device or installation, and may be able to optically interact with a material. The number of layers 102, 104 and the thickness of each layer 102, 104 are determined from the spectral attributes acquired from a spectroscopic analysis of a characteristic of the material being analyzed using a conventional spectroscopic instrument. The spectrum of interest of a given characteristic typically includes any number of different wavelengths.

It should be understood that the ICE core 100 depicted in FIG. 3 does not in fact represent any particular ICE core used to detect a specific characteristic of a given material, but is provided for purposes of illustration only. Consequently, the number of layers 102, 104 and their relative thicknesses, as shown in FIG. 3, bear no correlation to any particular material or characteristic thereof. Nor are the layers 102, 104 and their relative thicknesses necessarily drawn to scale, and therefore should not be considered limiting of the present disclosure.

In some embodiments, the material of each layer 102, 104 can be doped or two or more materials can be combined in a manner to achieve the desired optical characteristic. In addition to solids, the exemplary ICE core 100 may also contain liquids and/or gases, optionally in combination with solids, in order to produce a desired optical characteristic. In the case of gases and liquids, the ICE core 100 can contain a corresponding vessel (not shown), which houses the gases or liquids. Exemplary variations of the ICE core 100 may also include holographic optical elements, gratings, piezoelectric, light pipe, and/or acousto-optic elements, for example, that can create transmission, reflection, and/or absorptive properties of interest.

The multiple layers 102, 104 may exhibit different refractive indices. By properly selecting the materials of the layers 102, 104 and their relative thickness and spacing, the ICE core 100 may be configured to selectively transmit or reflect predetermined fractions of electromagnetic radiation at different wavelengths. Each wavelength is given a predetermined weighting or loading factor. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE core 100 as the physical representation of the IFT. The approximations convert the IFT into a structure based on known materials with constant refractive indices.

The weightings that the layers 102, 104 of the ICE core 100 apply at each wavelength may be set to the regression weightings described with respect to a known equation, data, or spectral signature. For instance, when electromagnetic radiation interacts with a material, unique physical and chemical information about the material are encoded in the electromagnetic radiation that is reflected from, transmitted through, or radiated from the material. This information is often referred to as the spectral "fingerprint" of the material. The ICE core 100 may be configured to have a wavelength dependent response function. For example, the ICE core 100 may be configured to apply a vector (e.g., a loaded regression vector, a loading vector, or the like) to the received electromagnetic radiation that is a wavelength dependent transmission function of the ICE core 100. The wavelength dependent transmission function of the ICE core 100 is dependent on the material refractive index of each layer, the number of layers 102, 104 and thickness of each layer 102, 104. For example, U.S. Pat. No. 9,019,501 describes the application of a vector to the received electromagnetic radiation using an ICE.

One type or variation of an ICE core 100 is a frequency selective surface (FSS) ICE core. The FSS ICE core is similar in some respects to the ICE core 100 described above, but instead of having a stack of dielectric thin film layers 102, 104, an FSS ICE core includes a single, periodically-patterned metallic thin film layer. Upon optically interacting with electromagnetic radiation, the FSS ICE core generates an optical processing function that is dependent on the shape of the FSS structure, the type of metal used for the thin film layer, and the thickness of the metal layer.

Another variation on the ICE core 100 is the capacitance-based nanomaterial detector. As described previously, the detection spectrum of the capacitance-based nanomaterial detector may be resonantly-tuned to the optical processing function that applies a weighting or loading factor to the electromagnetic radiation having optically interacted a material.

Figure 4:
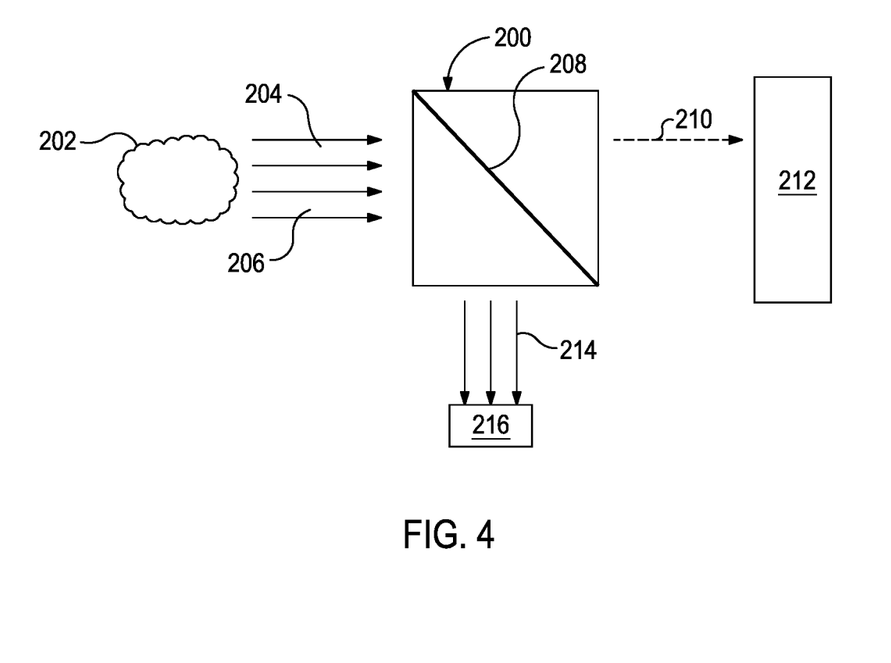
FIG. 4 illustrates a block diagram non-mechanistically illustrating an optical computing device, according to one or more embodiments.

Referring now to FIG. 4, illustrated is a block diagram that non-mechanistically illustrates how an optical computing device 200 is able to distinguish electromagnetic radiation related to a characteristic of interest from other electromagnetic radiation. As shown in FIG. 4, after being illuminated with incident electromagnetic radiation, a material 202 produces an output of electromagnetic radiation (e.g., interacted light), some of which is optically interacted light 204 corresponding to the characteristic of interest and some of which is background optically interacted light 206 corresponding to other characteristics of the material 202. In some embodiments, the material 202 may include one or more characteristics of interest that may correspond to the one or more analytes of the material 202.

Although not specifically shown, one or more processing elements may be employed in the optical computing device 200 in order to restrict the optical wavelengths and/or bandwidths of the system and thereby eliminate unwanted electromagnetic radiation existing in wavelength regions that have no importance. Such processing elements can be located anywhere along the optical train, but are typically employed directly after a light source, which provides the initial electromagnetic radiation.

The beams of optically interacted light 204,206 impinge upon the optical computing device 200, which contains an exemplary ICE 208 therein. In the illustrated embodiment, the ICE 208 may be configured to produce optically interacted light, for example, transmitted modified electromagnetic radiation 210 and reflected optically interacted light 214. In operation, the ICE 208 may be configured to distinguish the optically interacted light 204 from the background optically interacted light 206. As used herein, the term "modified electromagnetic radiation" refers to electromagnetic radiation that has optically interacted with both a material and an ICE in any order.

The transmitted modified electromagnetic radiation 210, which may be related to the characteristic of interest of the material 202, may be conveyed to a capacitance-based nanomaterial detector 212, as described herein, for analysis and quantification. In some embodiments, the capacitance-based nanomaterial detector 212 is configured to produce an output signal in the form of a voltage that corresponds to the particular characteristic of the material 202 (i.e., a characteristic of interest). In at least one embodiment, the signal produced by the capacitance-based nanomaterial detector 212 and the characteristic of a material 202 (e.g., concentration of an analyte) may be directly proportional. In other embodiments, the relationship may be a polynomial function, an exponential function, and/or a logarithmic function. The reflected optically interacted light 214, which may be related to other characteristics of the material 202, can be directed away from capacitance-based nanomaterial detector 212. In alternative configurations, the ICE 208 may be configured such that the reflected optically interacted light 214 can be related to the characteristic of interest, and the transmitted modified electromagnetic radiation 210 can be related to other characteristics in the material 202.

In some embodiments, the nano-sized materials of the capacitance-based nanomaterial detector 212 may be configured to have an absorption spectrum such that the output signal correlates positively or negatively to at least a portion of the modified electromagnetic radiation 210 generated by the ICE 208. For example, for a positive correlation, the voltage of the output signal may tend to increase as the concentration of the characteristic of interest increases. For a negative correlation, the voltage of the output signal may tend to decrease as the concentration of the characteristic of interest increases.

The illustrated system in FIG. 4 includes a second detector 216. The second detector 216 may, in some instances, be a second capacitance-based nanomaterial detector. In alternate embodiments, the second detector 216 may be, but is not limited to, a thermal detector such as a thermopile or photoacoustic detector, a semiconductor detector, a piezoelectric detector, a charge coupled device (CCD) detector, a video or array detector, a split detector, a quad detector, a photon detector (such as a photomultiplier tube), photodiodes, combinations thereof, or the like, or other detectors known to those skilled in the art.

In some embodiments, a second detector 216 may be present and arranged to detect the reflected optically interacted light 214. In other embodiments, the second detector 216 may be arranged to detect the optically interacted light 204,206 derived from the material 202 or electromagnetic radiation directed toward or before the material 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but are not limited to, intensity fluctuations in the electromagnetic radiation, interferent fluctuations (e.g., dust or other interferents passing in front of the electromagnetic radiation source), coatings on windows included with the optical computing device 200, combinations thereof, or the like. In some embodiments, a beam splitter (not shown) can be employed to split the electromagnetic radiation 204,206, and the transmitted or reflected electromagnetic radiation can then be directed to two or more ICE 208. That is, in such embodiments, the ICE 208 does not function as a type of beam splitter, as depicted in FIG. 4, and the transmitted or reflected electromagnetic radiation simply passes through the ICE 208, being computationally processed therein, before traveling to the capacitance-based nanomaterial detector 212.

Figure 5:
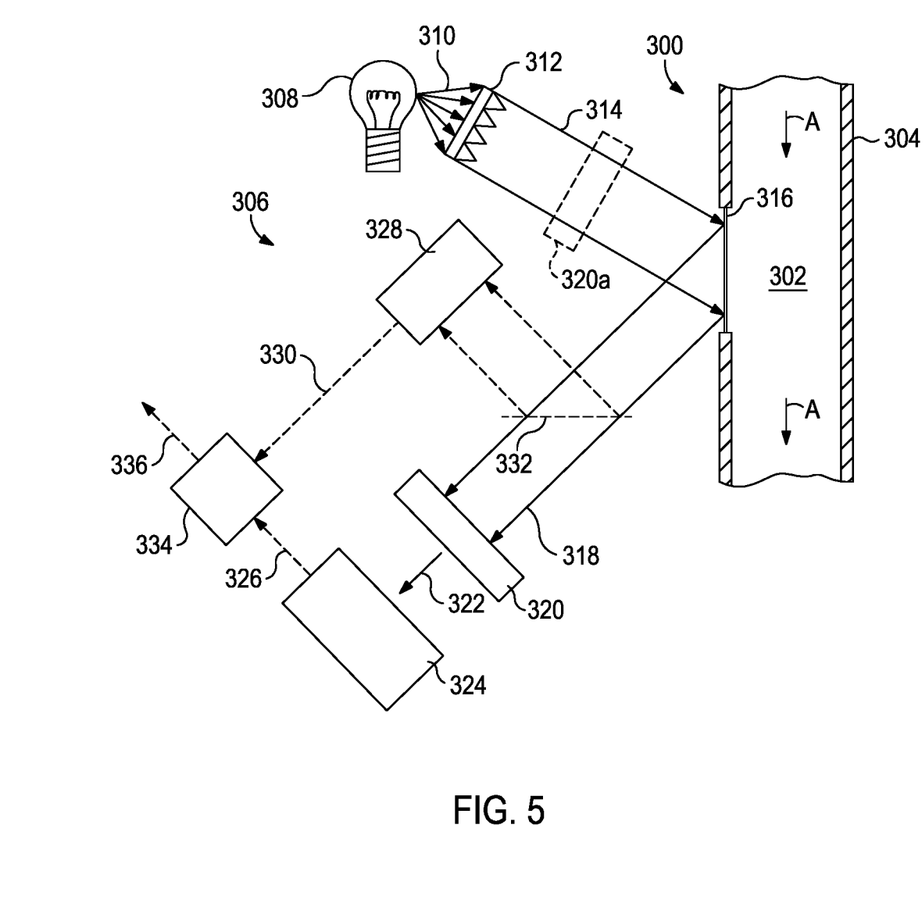
FIG. 5 illustrates an exemplary system for detecting a characteristic of a material using an optical computing device, according to one or more embodiments.

Referring now to FIG. 5, illustrated is an exemplary system 300 for monitoring or determining a particular characteristic of a material 302, according to one or more embodiments. In the illustrated embodiment, the material 302 may be within a flow path 304, although the material 302 need not be housed within a flow path 304 to comport with the embodiments described herein. The flow path 304 may be, for example, may be a portion of a sample chamber in a formation tester, or a portion of a wellbore, and the like. The material 302 may be flowing or otherwise moving in the flow path 304 may be flowing in the general direction indicated by the arrows A (i.e., upstream to downstream). It will be appreciated, however, that the flow path 304 may be in any direction, including a circular direction, without departing from the scope of the present disclosure.

The system 300 may include at least one optical computing device 306, which may be similar in some respects to the optical computing device 200 of FIG. 4. While not shown, the device 306 may be housed within a casing or housing configured to substantially protect the internal components of the device 306 from damage or contamination from the external environment. The housing may operate to mechanically couple or otherwise place in communication the device 306 to the flow path 304 with, for example, mechanical fasteners, brazing or welding techniques, adhesives, magnets, other fastening devices, combinations thereof, or the like.

As described in greater detail below, the optical computing device 306 may be useful in determining a particular characteristic of a material 302, such as one within the flow path 304. For example, the characteristic of the material 302 may be the concentration of an analyte present within the material 302. In some embodiments, the device 306 may include an electromagnetic radiation source 308 configured to emit or otherwise generate electromagnetic radiation 310.

The electromagnetic radiation source 308 may be any device capable of emitting or generating electromagnetic radiation, as defined herein. For example, the electromagnetic radiation source 308 may be a light bulb, a light emitting device (LED), a laser, a blackbody, a photonic crystal, an X-ray source, a gamma ray source, combinations thereof, or the like. In some embodiments, a lens 312 may be configured to collect or otherwise receive the electromagnetic radiation 310 and direct a beam 314 of electromagnetic radiation 310 toward the material 302 in an optical train. The lens 312 may be any type of optical device configured to transmit or otherwise convey the electromagnetic radiation 310 as desired. For example, the lens 312 may be a normal lens, a Fresnel lens, a diffractive optical element, a holographic graphical element, a mirror (e.g., a focusing mirror), a type of collimator, or any other electromagnetic radiation transmitting device known to those skilled in the art. In other embodiments, the lens 312 may be omitted from the device 306 and the electromagnetic radiation 310 may instead be conveyed toward the material 302 directly from the electromagnetic radiation source 308 in the optical train.

In one or more embodiments, the device 306 may also include a sampling window 316 arranged adjacent to or otherwise in contact with the material 302 for detection purposes. The sampling window 316 may be composed from a variety of transparent, rigid or semi-rigid materials that are configured to allow transmission of the electromagnetic radiation 310 therethrough. For example, the sampling window 316 may be composed of, but is not limited to, glasses, plastics, semi-conductors, crystalline materials, polycrystalline materials, hot or cold-pressed powders, combinations thereof, or the like. Although a sample window 316 is depicted as part of the system 300 in FIG. 5, it will be appreciated that a sample window 316 may be omitted from the system 300 and the electromagnetic radiation 310 may optically interact with a material 302 directly, without first passing through a sample window 316, without departing from the scope of the present disclosure.

As shown, after passing through the sampling window 316, the electromagnetic radiation 310 impinges upon and optically interacts with material 302 in the flow path 304. As a result, optically interacted radiation 318 is generated by and reflected from the material 302. Those skilled in the art, however, will readily recognize that alternative variations of the device 306 may allow the optically interacted radiation 318 to be generated by being transmitted, scattered, diffracted, absorbed, emitted, or re-radiated by and/or from the material 302, or one or more analytes of the material 302, without departing from the scope of the present disclosure.

The optically interacted radiation 318 generated by the interaction with the material 302 may be directed to or otherwise received by an ICE 320 arranged within the device 306. The ICE 320 may be a spectral component substantially similar to the ICE 100 described above with reference to FIG. 3. Accordingly, in operation the ICE 320 may be configured to receive the optically interacted radiation 318 and produce modified electromagnetic radiation 322 corresponding to a particular characteristic of interest of the material 302.

It should be noted, as previously discussed, that while FIG. 5 depicts the ICE 320 as receiving optically interacted radiation 318 from the material 302, the ICE 320 may be arranged at any point along the optical train of the device 306, without departing from the scope of the disclosure. For example, in one or more embodiments, the ICE 320a (shown in phantom) may be arranged within the optical train prior to the material 302 and the device 306 and equally obtain substantially the same results. Accordingly, the modified electromagnetic radiation 322 may be generated by optically interacting with at least one ICE and the material 302 in any order, without departing from the scope of the present disclosure. In other embodiments, the sampling window 316 may serve a dual purpose as both a transmission window and an ICE (i.e., a spectral component). In yet other embodiments, the ICE 320 may generate the modified electromagnetic radiation 322 through reflection, instead of transmission therethrough.

Moreover, while only one ICE 320 is shown in the device 306, embodiments are contemplated herein which include the use of at least two ICE components in the device 306 configured to cooperatively determine the characteristic of interest in the material 302. For example, two or more ICE components may be arranged in series or parallel within the device 306 at any point along the optical train and configured to receive the electromagnetic radiation 310 or optically interacted radiation 318 to enhance sensitivities and detector limits of the device 306. In other embodiments, two or more ICE components may be arranged on a movable assembly, such as a rotating disc or an oscillating linear array, which moves such that the individual ICE components are able to be exposed to or otherwise optically interact with electromagnetic radiation 310 for a distinct brief period of time. The two or more ICE components in any of these embodiments may be configured to be either associated or disassociated with the characteristic of interest in the material 302.

In some embodiments, it may be desirable to monitor more than one characteristic of interest at a time using the device 306. In such embodiments, various configurations for multiple ICE components may be used, where each ICE component is configured to detect a particular and/or distinct characteristic of interest corresponding, for example, to a characteristic of the material 302. In some embodiments, the characteristic of interest may be analyzed sequentially using multiple ICE components that in which a single beam of optically interacted radiation 318 is reflected from or transmitted through the material 302. In some embodiments, multiple ICE 320 components may be arranged on a rotating disc, where the individual ICE components are only exposed to the beam of optically interacted radiation 318 for a short time. Advantages of this approach may include the ability to analyze multiple characteristics of interest of a material 302 (or multiple types of materials of interest 302) using a single device 306 and the opportunity to assay additional characteristics simply by adding additional ICE components corresponding to those additional characteristics or corresponding to different types of materials of interest 302. Again, it should be noted, that the one or more ICE components may be located before, after, or before and after (i.e., where multiple ICE components are used) the material 302, without departing from the scope of the present disclosure.

In other embodiments, multiple devices 306 may be placed at a single location along the flow path 304, where each device 306 contains a unique ICE that is configured to detect a particular characteristic of interest of the material 302. In such embodiments, a beam splitter can divert a portion of the optically interacted radiation 318 being reflected by, emitted from, or transmitted through the material 302 and into each device 306. Each device 306, in turn, can be coupled to a corresponding capacitance-based nanomaterial detector or capacitance-based nanomaterial detector array that is configured to detect and analyze an output of electromagnetic radiation from the respective device 306. Parallel configurations of optical computing devices 306 may be particularly beneficial for applications that require low power inputs and/or no moving parts.

The modified electromagnetic radiation 322 generated by the ICE 320 may subsequently be conveyed to a capacitance-based nanomaterial detector 324 for quantification of the signal.

In some embodiments, the capacitance-based nanomaterial detector 324 may be configured to produce an output signal 326 in real-time or near real-time in the form of a voltage (or current) that corresponds, positively or negatively, to the particular characteristic of interest of the material 302 (i.e., an output signal 326 indicative of the characteristic of interest of the material). As such, the output signal 326 produced by the capacitance-based nanomaterial detector 324 and the characteristic of interest may have a relationship that is directly proportional or may correspond to a polynomial function, an exponential function, a logarithmic function, a combination thereof, or the like.

In some embodiments, the device 306 may include a second detector 328, which may be any device capable of detecting electromagnetic radiation. The second detector 328, which may be similar to the second detector 216 of FIG. 3, may be used to detect radiating deviations stemming from the electromagnetic radiation source 308. Undesirable variations may occur in the intensity of the electromagnetic radiation 310 due to a wide variety of reasons and potentially causing various negative effects on the output of the device 306. These negative effects may be particularly detrimental for measurements taken over a period of time. In some embodiments, the variations may occur as a result of a build-up of film or material on the sampling window 316, which may have the effect of reducing the amount and quality of light ultimately reaching the first capacitance-based nanomaterial detector 324. Without proper compensation, such radiation deviations may result in false readings and the output signal 326 would no longer be primarily or accurately related to the characteristic of interest.

To compensate for these variations in light intensity, the second detector 328 may be configured to generate a compensating signal 330 generally indicative of the radiation deviations of the electromagnetic radiation source 308, and thereby normalize the output signal 326 generated by the first capacitance-based nanomaterial detector 324. As illustrated, the second detector 328 may be configured to receive a portion of the optically interacted radiation 318 via a beam splitter 332 in order to detect these variations. In other embodiments, however, the second detector 328 may be arranged to receive electromagnetic radiation from any portion of the optical train in the device 306 in order to detect the variations in source intensity, without departing from the scope of the disclosure.

In some applications, the output signal 326 and the compensating signal 330 may be conveyed to or otherwise received by a signal processor 334 communicably coupled to both the capacitance-based nanomaterial detectors 324, 328. The signal processor 334 may be a computer including a non-transitory machine-readable medium, and may be configured to computationally combine the compensating signal 330 with the output signal 326 in order to normalize the output signal 326 in view of any light source intensity variations detected by the second detector 328 and produce a resulting output signal 336. In some embodiments, computationally combining the output and compensating signals 326, 330 may entail computing a ratio of the two signals 326, 330. For example, the concentration or magnitude of each characteristic of interest determined using the optical computing device 306 may be fed into an algorithm run by the signal processor 334.

In real-time or near real-time, the signal processor 334 may be configured to provide the resulting output signal 336 corresponding, positively or negatively, to a characteristic of interest in the material 302. The resulting output signal 336 may be readable by an operator who can consider the results and make proper adjustments or take appropriate action, if needed, based upon output signal related to the material 302 (e.g., a concentration of the material 302 or a concentration of a characteristic of the material 302). In some embodiments, the resulting signal output 336 may be conveyed, either wired or wirelessly, to an operator for consideration. In other embodiments, the resulting output signal 336 of the characteristic of interest may be recognized by the signal processor 334 as being within or without an acceptable limit range for a particular operation and may alert the operator of an out of range reading so appropriate corrective action may be taken, or otherwise autonomously undertake the appropriate corrective action such that the resulting output signal 336 returns to a value within the predetermined or preprogrammed range of suitable operation.

Figure 6:
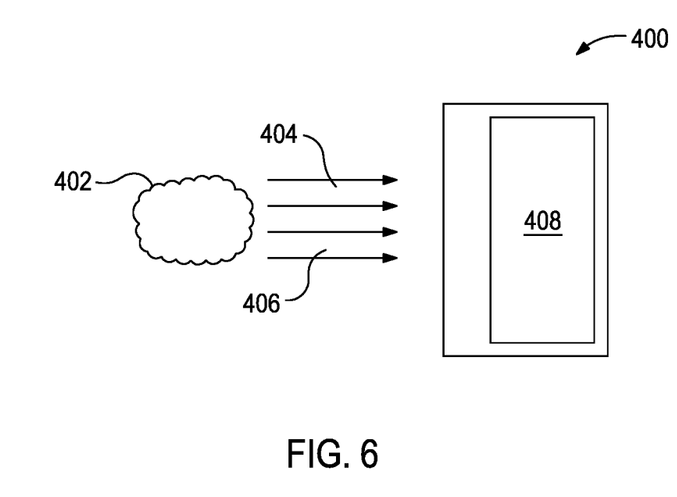
FIG. 6 illustrates a block diagram non-mechanistically illustrating an optical computing device, according to one or more embodiments.

Referring now to FIG. 6, illustrated is a block diagram that non-mechanistically illustrates how an optical computing device 400 is able to distinguish electromagnetic radiation related to a characteristic of interest from other electromagnetic radiation. As shown in FIG. 6, after being illuminated with incident electromagnetic radiation, a material 402 produces an output of electromagnetic radiation (e.g., optically interacted light), some of which is electromagnetic radiation 404 corresponding to the characteristic of interest and some of which is background electromagnetic radiation 406 corresponding to other characteristics of the material 402. In some embodiments, the material 402 may include one or more characteristics of interest that may correspond to the one or more analytes of the material 402.

Although not specifically shown, one or more processing elements may be employed in the optical computing device 400 in order to restrict the optical wavelengths and/or bandwidths of the system and thereby eliminate unwanted electromagnetic radiation existing in wavelength regions that have no importance. Such processing elements can be located anywhere along the optical train, but are typically employed directly after a light source, which provides the initial electromagnetic radiation.

The beams of electromagnetic radiation 404,406 impinge upon the optical computing device 400, which contains an exemplary capacitance-based nanomaterial ICE/detector 408 therein. In the illustrated embodiment, the nano-sized materials of the capacitance-based nanomaterial ICE/detector 408 may be chosen to have a desired wavelength dependent response function corresponding to the characteristic of interest of the material 402. For example, the absorption spectrum may be a wavelength dependent response function that applies a vector (e.g., a loaded regression vector, a loading vector, or the like) to the electromagnetic radiation 404 corresponding to the characteristic of interest. For example, U.S. Pat. No. 9,019,501 describes the application of a vector to the received electromagnetic radiation using an ICE, where the absorption spectrum of the capacitance-based nanomaterial ICE/detector 408 is configured via resonant enhancement to apply at each wavelength a set to the regression weightings described with respect to a known equation, or data, or spectral signature such that the intensity of each wavelength detected by the capacitance-based nanomaterial ICE/detector 408 is related to the characteristic of interest.

In operation, the desired absorption spectrum may be chosen so as to distinguish the electromagnetic radiation 404 from the background electromagnetic radiation 406 using resonance tuning principles described herein. The capacitance-based nanomaterial ICE/detector 408 may also analyze and quantify the electromagnetic radiation 404 corresponding to the characteristic of interest of the material 402 (e.g., based on the absorption spectrum).

The capacitance-based nanomaterial ICE/detector 408 may be configured to produce an output signal in the form of a voltage that corresponds to the particular characteristic of the material 402. In at least one embodiment, the signal produced by the capacitance-based nanomaterial ICE/detector 408 may be directly proportional to the characteristic of a material 402 (e.g., concentration of an analyte). In other embodiments, the relationship may be a polynomial function, an exponential function, and/or a logarithmic function.

Figure 7:
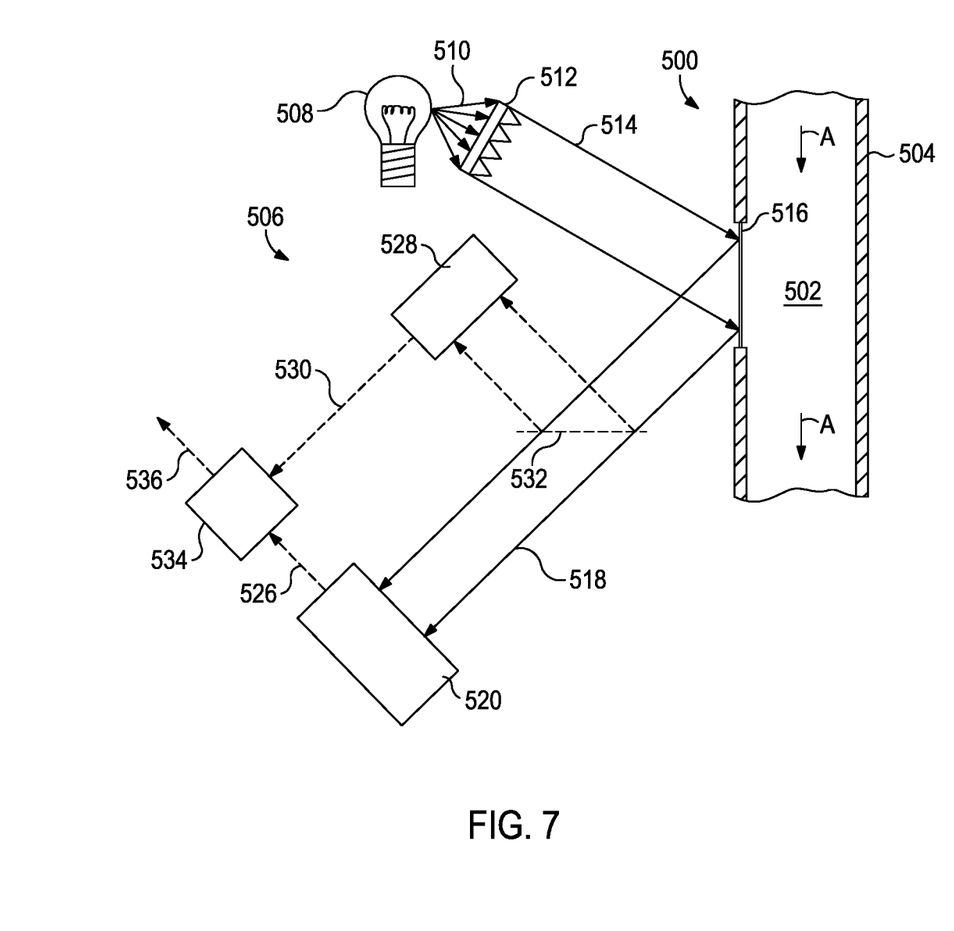
FIG. 7 illustrates a block diagram non-mechanistically illustrating an optical computing device, according to one or more embodiments.

Referring now to FIG. 7, illustrated is an exemplary system 500 for monitoring or determining a particular characteristic of a material 502, according to one or more embodiments. In the illustrated embodiment, the material 502 may be within a flow path 504, although the material 502 need not be housed within a flow path 504 to comport with the embodiments described herein. The flow path 504 may be, for example, may be a portion of a sample chamber in a formation tester, or a portion of a wellbore, and the like. The material 502 may be flowing or otherwise moving in the flow path 504 may be flowing in the general direction indicated by the arrows A (i.e., upstream to downstream). It will be appreciated, however, that the flow path 504 may be in any direction, including a circular direction, without departing from the scope of the present disclosure.

The system 500 may include at least one optical computing device 506, which may be similar in some respects to the optical computing device 200 of FIG. 4. While not shown, the device 506 may be housed within a casing or housing configured to substantially protect the internal components of the device 506 from damage or contamination from the external environment. The housing may operate to mechanically couple or otherwise place in communication the device 506 to the flow path 504 with, for example, mechanical fasteners, brazing or welding techniques, adhesives, magnets, other fastening devices, combinations thereof, or the like.

The optical computing device 506 may be useful in determining a particular characteristic of a material 502 as described herein. In some embodiments, the device 506 may include an electromagnetic radiation source 508 configured to emit or otherwise generate electromagnetic radiation 510. The electromagnetic radiation source 508 may be any device capable of emitting or generating electromagnetic radiation, as defined herein. In some embodiments, a lens 512 may be configured to collect or otherwise receive the electromagnetic radiation 510 and direct a beam 514 of electromagnetic radiation 510 toward the material 502 in an optical train. In other embodiments, the lens 512 may be omitted from the device 506 and the electromagnetic radiation 510 may instead be conveyed toward the material 502 directly from the electromagnetic radiation source 508 in the optical train.

In one or more embodiments, the device 506 may also include a sampling window 516 arranged adjacent to or otherwise in contact with the material 502 for detection purposes. Although a sample window 516 is depicted as part of the system 500 in FIG. 7, it will be appreciated that a sample window 516 may be omitted from the system 500 and the electromagnetic radiation 510 may optically interact with a material 502 directly, without first passing through a sample window 516, without departing from the scope of the present disclosure.

As shown, after passing through the sampling window 516, the electromagnetic radiation 510 impinges upon and optically interacts with material 502 in the flow path 504. As a result, optically interacted radiation 518 is generated by and reflected from the material 502. Those skilled in the art, however, will readily recognize that alternative variations of the device 506 may allow the optically interacted radiation 518 to be generated by being transmitted, scattered, diffracted, absorbed, emitted, or re-radiated by and/or from the material 502, or one or more analytes of the material 502, without departing from the scope of the present disclosure.

The optically interacted radiation 518 generated by the interaction with the material 502 may be directed to or otherwise received by a capacitance-based nanomaterial ICE/detector 520 described herein (e.g., being the same or similar to capacitance-based nanomaterial ICE/detector 408) arranged within the device 506. While only one capacitance-based nanomaterial ICE/detector 520 is shown in the device 506, embodiments are contemplated herein which include the use of at least two capacitance-based nanomaterial ICE/detectors in the device 506 configured to cooperatively determine the characteristic of interest in the material 502. For example, two or more capacitance-based nanomaterial ICE/detectors may be arranged in parallel within the device 506 at any point along the optical train and configured to receive the optically interacted radiation 518 to enhance sensitivities and detector limits of the device 506. In other embodiments, two or more capacitance-based nanomaterial ICE/detectors may be arranged on a movable assembly, such as a rotating disc or an oscillating linear array, which moves such that the individual capacitance-based nanomaterial ICE/detectors are able to be exposed to or otherwise optically interact with electromagnetic radiation 510 for a distinct brief period of time. The two or more capacitance-based nanomaterial ICE/detectors in any of these embodiments may be configured to be either associated or disassociated with the characteristic of interest in the material 502. In some embodiments, multiple capacitance-based nanomaterial ICE/detectors 520 may be arranged on a rotating disc, where the individual ICE components are only exposed to the beam of optically interacted radiation 518 for a short time.

In other embodiments, multiple devices 506 may be placed at a single location along the flow path 504, where each device 506 contains a unique capacitance-based nanomaterial ICE/detector 420 that is configured to detect a particular characteristic of interest of the material 502. In such embodiments, a beam splitter can divert a portion of the optically interacted radiation 518 being reflected by, emitted from, or transmitted through the material 502 and into each device 506. Each device 506 detects and analyzes an output of electromagnetic radiation from the respective device 506. Parallel configurations of optical computing devices 506 may be particularly beneficial for applications that require low power inputs and/or no moving parts.

In some embodiments, the device 506 may include a second detector 528, which may optionally be a capacitance-based nanomaterial detector similar to the first capacitance-based nanomaterial detector 520 or may be another type of detector (e.g., similar to the second detector 216 of FIG. 4). The second detector 528 may be used to detect radiating deviations stemming from the electromagnetic radiation source 508. Undesirable variations may occur in the intensity of the electromagnetic radiation 510 due to a wide variety of reasons and potentially causing various negative effects on the output of the device 506. These negative effects may be particularly detrimental for measurements taken over a period of time. In some embodiments, the variations may occur as a result of a build-up of film or material on the sampling window 516, which may have the effect of reducing the amount and quality of light ultimately reaching the first capacitance-based nanomaterial detector 520. Without proper compensation, such radiation deviations may result in false readings and the output signal 526 would no longer be primarily or accurately related to the characteristic of interest.

To compensate for these variations in light intensity, the second detector 528 may be configured to generate a compensating signal 530 generally indicative of the radiation deviations of the electromagnetic radiation source 508, and thereby normalize the output signal 526 generated by the first capacitance-based nanomaterial detector 520. As illustrated, the second detector 528 may be configured to receive a portion of the optically interacted radiation 518 via a beam splitter 532 in order to detect these variations. In other embodiments, however, the second detector 528 may be arranged to receive electromagnetic radiation from any portion of the optical train in the device 506 in order to detect the variations in source intensity, without departing from the scope of the disclosure.

In some applications, the output signal 526 and the compensating signal 530 may be conveyed to or otherwise received by a signal processor 534 communicably coupled to both the capacitance-based nanomaterial detectors 520 and the second detector 528. The signal processor 534 may be a computer including a non-transitory machine-readable medium, and may be configured to computationally combine the compensating signal 530 with the output signal 526 in order to normalize the output signal 526 in view of any light source intensity variations detected by the second detector 528 and produce a resulting output signal 536. In some embodiments, computationally combining the output and compensating signals 526, 530 may entail computing a ratio of the two signals 526, 530. For example, the concentration or magnitude of each characteristic of interest determined using the optical computing device 506 may be fed into an algorithm run by the signal processor 534.

In real-time or near real-time, the signal processor 534 may be configured to provide the resulting output signal 536 corresponding to a characteristic of interest in the material 502. The resulting output signal 536 may be readable by an operator who can consider the results and make proper adjustments or take appropriate action, if needed, based upon output signal related to the material 502 (e.g., a concentration of the material 502 or a concentration of a characteristic of the material 502). In some embodiments, the resulting signal output 536 may be conveyed, either wired or wirelessly, to an operator for consideration. In other embodiments, the resulting output signal 536 of the characteristic of interest may be recognized by the signal processor 534 as being within or without an acceptable limit range for a particular operation and may alert the operator of an out of range reading so appropriate corrective action may be taken, or otherwise autonomously undertake the appropriate corrective action such that the resulting output signal 536 returns to a value within the predetermined or preprogrammed range of suitable operation.

In some embodiments, the magnitude of the characteristic of interest determined using an optical computing device 200,300,400,500 described herein may be fed into an algorithm operating under computer control. The algorithm may be configured to determine whether the material or characteristic of interest of the material is in programmed acceptable limits, which may be narrowed depending on a particular operation. In some embodiments, the algorithm can produce an output that is readable by an operator who can manually take appropriate action, if needed, based upon the reported output. In some embodiments, the algorithm may direct the operator as to how to take a corrective action (e.g., how to bring the amount of the material or characteristic of interest of the material within acceptable limits). In other embodiments, the algorithm can take proactive process control (e.g., halt operations, alter a composition comprising the material or characteristic of interest of the material, and the like). It is to be recognized that the algorithm (e.g., an artificial neural network) can be trained using materials of predetermined characteristics of interest, and thereby generating a virtual library. As the virtual library available to the artificial neural network becomes larger, the neural network can become more capable of accurately predicting the material or characteristic of interest of the material. Furthermore, with sufficient training, the artificial neural network can more accurately predict the material or characteristic of interest of the material, even in the presence of unknown analytes.

In some embodiments, the data collected using one or more optical computing devices 200,300,400,500 described herein may be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system may also allow remote monitoring to take place. Automated control with a long-range communication system can further facilitate the performance of remote job operations. In particular, an artificial neural network can be used in some embodiments to facilitate the performance of remote job operations. That is, remote job operations may be conducted automatically in some embodiments. In other embodiments, however, remote job operations can occur under direct operator control, where the operator is not at the job site (e.g., via wireless technology).

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable programmable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM, and flash EPROM.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Embodiments described herein include Embodiments A, B, C, and D.

Embodiment A is an optical computing device comprising: a light source that emits electromagnetic radiation into an optical train that extends from the light source to a capacitance-based nanomaterial detector that comprises one or more nano-sized materials that have an absorption spectrum; a material and an integrated computational element (ICE) core positioned in the optical train to optically interact with the electromagnetic radiation, thereby generate modified electromagnetic radiation, wherein the material includes a characteristic of interest and the ICE core applies a vector to the electromagnetic radiation that is related to the characteristic of interest, and wherein the capacitance-based nanomaterial detector receives the modified electromagnetic radiation and generates an output signal indicative of the characteristic of interest.

Embodiment A may optionally include one or more of the following: Element 1: wherein the output signal of the capacitance-based nanomaterial detector positively correlates to the characteristic of interest; Element 2: wherein the output signal of the capacitance-based nanomaterial detector negatively correlates to the characteristic of interest; Element 3: wherein the capacitance-based nanomaterial detector is a first detector, and wherein the optical computing device further comprises a second detector and a beam splitter, the beam splitter being positioned in the optical train to receive the modified electromagnetic radiation and direct the modified electromagnetic radiation to the first and second detectors; Element 4: Element 3 and wherein the second detector is a second capacitance-based nanomaterial detector; Element 5: wherein the one or more nano-sized materials comprise at least one selected from the group consisting of Si, Ge, $Si_xGe_y$, (x+y=1, 0<x<1), GaAs, and GaSb; and Element 6: wherein the one or more nano-sized materials comprise at least one nanoparticle having a shape selected from the group consisting of a film, a wire, a rod, a tube, a stars, and a disc. Exemplary combinations may include, but are not limited to, Elements 1 or 2 in combination with Element 3 and optionally Element 4; Elements 5 and/or 6 in combination with Element 1 or Element 2; Elements 5 and/or 6 in combination with Element 3 and optionally Element 4 and optionally further in combination with Elements 1 or 2; and Elements 5 and 6 in combination.

Embodiment B is a method comprising: emitting electromagnetic radiation with a light source into an optical train that extends from the light source to a capacitance-based nanomaterial detector comprising one or more nano-sized materials configured to have an absorption spectrum; optically interacting the electromagnetic radiation with a material and an integrated computational element (ICE) core positioned in the optical train, thereby producing modified electromagnetic radiation, wherein the material includes a characteristic of interest and the ICE core applies a vector to the electromagnetic radiation that is related to the characteristic of interest; receiving the modified electromagnetic radiation with the capacitance-based nanomaterial detector; and generating an output signal from the capacitance-based nanomaterial detector indicative of the characteristic of interest.

Embodiment B may optionally include one or more of the following: Element 1; Element 2; Element 5; Element 6; Element 7: wherein the capacitance-based nanomaterial detector is a first detector, and wherein the method further comprises directing the modified electromagnetic radiation with a beam splitter to the first detector and a second detector; Element 8: Element 7 and wherein the second detector is a second capacitance-based nanomaterial detector. Exemplary combinations may include, but are not limited to, Elements 5 and/or 6 in combination with Element 7 and optionally Element 8; Elements 1 or 2 in combination with Element 7 and optionally Element 8; and Elements 1 or 2 in combination with Elements 5 and/or 6 and optionally in further combination with Element 7 and optionally Element 8.

Embodiment C is an optical computing device, comprising: a light source that emits electromagnetic radiation into an optical train extending from the light source to a capacitance-based nanomaterial detector; a material having a characteristic of interested and being positioned in the optical train to optically interact with the electromagnetic radiation and produce optically interacted light; and the capacitance-based nanomaterial detector comprising one or more nano-sized materials configured to have a resonantly-tuned absorption spectrum and being configured to receive the optically interacted light, apply a vector related to the characteristic of interest to the optically interacted light using the resonantly-tuned absorption spectrum, and generate an output signal indicative of the characteristic of interest.

Embodiment D is a method comprising: emitting electromagnetic radiation with a light source into an optical train that extends from the light source to a capacitance-based nanomaterial detector comprising one or more nano-sized materials configured to have a resonantly-tuned absorption spectrum; optically interacting the electromagnetic radiation with a material having a characteristic of interest and being positioned in the optical train, thereby producing optically interacted light; receiving the optically interacted light with the capacitance-based nanomaterial detector; apply a vector related to the characteristic of interest to the optically interacted light using the resonantly-tuned absorption spectrum; and generating an output signal from the capacitance-based nanomaterial detector indicative of the characteristic of interest.

Embodiments C and D may optionally include one or more of the following: Element 5; Element 6; Element 9: wherein the output signal of the capacitance-based nanomaterial detector positively correlates to the characteristic of interest; Element 10: wherein the absorption spectrum of the capacitance-based nanomaterial detector is resonantly-tuned to negatively correlate to the characteristic of interest; Element 11: wherein the capacitance-based nanomaterial detector is a first detector, and wherein the optical computing device further comprises a second detector and a beam splitter, the beam splitter being positioned in the optical train to receive the optically interacted light and direct the optically interacted light to the first and second detectors; Element 12: Element 11 and wherein the second detector is a second capacitance-based nanomaterial detector comprising one or more nano-sized materials configured to have a resonantly-tuned absorption spectrum and being configured to receive the optically interacted light, apply a vector related to the characteristic of interest to the optically interacted light using the resonantly-tuned absorption spectrum, and generate an output signal indicative of and negatively correlated to the characteristic of interest, and wherein the first detector is positively correlated to the characteristic of interest. Exemplary combinations may include, but are not limited to, Elements 5 and/or 6 in combination with Element 11 and optionally Element 12 and optionally in further combination with Elements 9 or 10; Elements 5 and/or 6 in combination with Elements 9 or 10; and Elements 5 and 6 in combination.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An optical computing device, comprising:
   a light source that emits electromagnetic radiation into an optical train that extends from the light source to a capacitance-based nanomaterial detector that comprises one or more nano-sized materials that have an absorption spectrum;
   a material and an integrated computational element (ICE) core positioned in the optical train to optically interact with the electromagnetic radiation, thereby generating modified electromagnetic radiation,
   wherein the material includes a characteristic of interest and the ICE core applies a vector to the electromagnetic radiation that is related to the characteristic of interest,
   wherein the capacitance-based nanomaterial detector receives the modified electromagnetic radiation and generates an output signal indicative of the characteristic of interest, and
   wherein the absorption spectrum of the one or more nano-sized materials corresponds to a spectrum of the modified electromagnetic radiation.

2. The optical computing device of claim 1, wherein the output signal of the capacitance-based nanomaterial detector positively correlates to the characteristic of interest.

3. The optical computing device of claim 1, wherein the output signal of the capacitance-based nanomaterial detector negatively correlates to the characteristic of interest.

4. The optical computing device of claim 1, wherein the capacitance-based nanomaterial detector is a first detector, and wherein the optical computing device further comprises a second detector and a beam splitter, the beam splitter being positioned in the optical train direct the modified electromagnetic radiation to the first and second detectors.

5. The optical computing device of claim 4, wherein the second detector is a second capacitance-based nanomaterial detector.

6. The optical computing device of claim 1, wherein the one or more nano-sized materials comprise at least one selected from the group consisting of Si, Ge, $Si_xGe_y$ (x+y=1, 0<x<1), GaAs, and GaSb.

7. The optical computing device of claim 1, wherein the one or more nano-sized materials comprise at least one nanoparticle having a shape selected from the group consisting of a film, a wire, a rod, a tube, a stars, and a disc.

8. A method comprising:
emitting electromagnetic radiation with a light source into an optical train that extends from the light source to a capacitance-based nanomaterial detector comprising one or more nano-sized materials configured to have an absorption spectrum;
optically interacting the electromagnetic radiation with a material and an integrated computational element (ICE) core positioned in the optical train, thereby producing modified electromagnetic radiation, wherein the material includes a characteristic of interest and the ICE core applies a vector to the electromagnetic radiation that is related to the characteristic of interest;
receiving the modified electromagnetic radiation with the capacitance-based nanomaterial detector; and
generating an output signal from the capacitance-based nanomaterial detector indicative of the characteristic of interest,
wherein the absorption spectrum of the one or more nano-sized materials corresponds to a spectrum of the modified electromagnetic radiation.

9. The method of claim 8, wherein the capacitance-based nanomaterial detector is a first detector, and wherein the method further comprises directing the modified electromagnetic radiation with a beam splitter to the first detector and a second detector.

10. The method of claim 9, wherein the second detector is a second capacitance-based nanomaterial detector.

11. An optical computing device, comprising:
a light source that emits electromagnetic radiation into an optical train extending from the light source to a capacitance-based nanomaterial detector;
a material having a characteristic of interest and being positioned in the optical train to optically interact with the electromagnetic radiation and produce optically interacted light; and
the capacitance-based nanomaterial detector comprising one or more nano-sized materials configured to have a resonantly-tuned absorption spectrum and being configured to receive the optically interacted light, apply a vector related to the characteristic of interest to the optically interacted light using the resonantly-tuned absorption spectrum, and generate an output signal indicative of the characteristic of interest,
wherein the resonantly-tuned absorption spectrum corresponds to a spectrum of the optically interacted light.

12. The optical computing device of claim 11, wherein the output signal of the capacitance-based nanomaterial detector positively correlates to the characteristic of interest.

13. The optical computing device of claim 11, wherein the absorption spectrum of the capacitance-based nanomaterial detector is resonantly-tuned to negatively correlate to the characteristic of interest.

14. The optical computing device of claim 11, wherein the capacitance-based nanomaterial detector is a first detector, and wherein the optical computing device further comprises a second detector and a beam splitter, the beam splitter being positioned in the optical train to receive the optically interacted light and direct the optically interacted light to the first and second detectors.

15. The optical computing device of claim 14, wherein the second detector is a second capacitance-based nanomaterial detector comprising one or more nano-sized materials configured to have a resonantly-tuned absorption spectrum and being configured to receive the optically interacted light, apply a vector related to the characteristic of interest to the optically interacted light using the resonantly-tuned absorption spectrum, and generate an output signal indicative of and negatively correlated to the characteristic of interest, and wherein the first detector is positively correlated to the characteristic of interest.

16. The optical computing device of claim 11, wherein the one or more nano-sized materials comprise at least one selected from the group consisting of Si, Ge, $Si_xGe_y$ (x+y=1, 0<x<1), GaAs, and GaSb.

17. The optical computing device of claim 11, wherein the one or more nano-sized materials comprise at least one nanoparticle having a shape selected from the group consisting of a film, a wire, a rod, a tube, a stars, and a disc.

18. A method comprising:
emitting electromagnetic radiation with a light source into an optical train that extends from the light source to a capacitance-based nanomaterial detector comprising one or more nano-sized materials configured to have a resonantly-tuned absorption spectrum;
optically interacting the electromagnetic radiation with a material having a characteristic of interest and being positioned in the optical train, thereby producing optically interacted light;
receiving the optically interacted light with the capacitance-based nanomaterial detector;
apply a vector related to the characteristic of interest to the optically interacted light using the resonantly-tuned absorption spectrum; and
generating an output signal from the capacitance-based nanomaterial detector indicative of the characteristic of interest,
wherein the resonantly-tuned absorption spectrum corresponds to a spectrum of the optically interacted light.

* * * * *